(12) United States Patent
Wilks et al.

(10) Patent No.: US 8,697,917 B2
(45) Date of Patent: Apr. 15, 2014

(54) METHODS AND SYSTEMS FOR CO-PRODUCING A LOW-METHANOL CONTENT ACETONE

(71) Applicant: Kellogg Brown & Root LLC, Houston, TX (US)

(72) Inventors: Theodor R. Wilks, Sugar Land, TX (US); Manish Bhargava, Katy, TX (US); Eric Wing-Tak Wong, Houston, TX (US)

(73) Assignee: Kellogg Brown & Root LLC, Houston, TX (US)

( * ) Notice: Subject to any disclaimer, the term of this patent is extended or adjusted under 35 U.S.C. 154(b) by 14 days.

(21) Appl. No.: 13/622,268

(22) Filed: Sep. 18, 2012

(65) Prior Publication Data

US 2013/0072723 A1  Mar. 21, 2013

Related U.S. Application Data (60) Provisional application No. 61/536,522, filed on Sep. 19, 2011, provisional application No. 61/536,529, filed on Sep. 19, 2011.

(51) Int. Cl.
*C07C 45/80* (2006.01)
*B01J 19/00* (2006.01)

(52) U.S. Cl.
USPC .......................................... 568/408; 422/187

(58) Field of Classification Search
USPC .......................................... 568/408; 422/187
See application file for complete search history.

(56) References Cited

U.S. PATENT DOCUMENTS 5,777,180 A * 7/1998 June et al. .................. 568/728
6,372,021 B1 * 4/2002 Boggs et al. ................ 95/92

* cited by examiner

*Primary Examiner* — Sikarl Witherspoon
(74) *Attorney, Agent, or Firm* — Gary M. Machetta (57) ABSTRACT

Methods and systems for producing low methanol concentration acetone are provided. The method can include oxidizing and cleaving cumene to produce a crude acetone product. The crude acetone product can be neutralized in a neutralization unit to produce a neutralized crude acetone product. The neutralized crude acetone product can be fractionated in an acetone fractionation column to produce an acetone product and an acetone bottoms product. Methanol can be removed from the acetone bottoms product to produce a methanol-depleted product. The methanol-depleted product can be introduced to the neutralization unit, a dephenolation unit, or both.

20 Claims, 3 Drawing Sheets

METHODS AND SYSTEMS FOR CO-PRODUCING A LOW-METHANOL CONTENT ACETONE

CROSS-REFERENCE TO RELATED APPLICATIONS

This application claims priority to U.S. Provisional Patent Applications having Ser. No. 61/536,529 and 61/536,522, both filed on Sep. 19, 2011, which are both incorporated by reference herein.

BACKGROUND

1. Field

Embodiments described herein generally relate to methods and systems for producing phenol and acetone from cumene. More particularly, such embodiments relate to methods and systems for producing acetone having a reduced concentration of methanol.

2. Description of the Related Art

Phenol and acetone are produced in various processes, the most common of which is known variously as the Hock Process, the Hock and Lang Process, or the cumene-to-phenol process, among others. This process begins with the oxidation of cumene (isopropyl benzene) to form cumene hydroperoxide (CHP). The CHP is then cleaved in the presence of an acid catalyst to form phenol and acetone. The phenol and acetone stream is subsequently neutralized in a salt solution and thereafter fractionated to recover the end-products phenol and acetone.

The cleavage and oxidation stages of the cumene-to-phenol process can increase the concentration of methanol in the production stream. In some processes that can use the acetone product it can be desirable to minimize the methanol content in the acetone product. For example, in the production of bis-phenol-A (BPA) from the acetone product, reduction of the methanol concentration can be beneficial because the methanol significantly reduces the life of the resin catalyst used to produce the BPA from phenol and acetone. However, the methanol can be relatively difficult to remove using traditional distillation systems, as the methanol can combine with acetone to form azeotropes with low boiling points. For example, in a typical acetone distillation column, the acetone product can have a residual methanol content of about 150 ppm to about 250 ppm. Such high residual methanol content in the acetone product can reduce the life of the BPA catalyst resin, resulting in increased costs of BPA production.

There is a need, therefore, for improved systems and methods for producing acetone having a reduced concentration of methanol.

DETAILED DESCRIPTION

Methods and systems for producing low methanol concentration acetone are provided. The method can include oxidizing and cleaving cumene to produce a crude acetone product. The crude acetone product can be neutralized in a neutralization unit to produce a neutralized crude acetone product. The neutralized crude acetone product can be fractionated in an acetone fractionation column to produce an acetone product and an acetone bottoms product. Methanol can be removed from the acetone bottoms product to produce a methanol-depleted product. The methanol-depleted product can be introduced to the neutralization unit, a dephenolation unit, or both.

Figure 1:
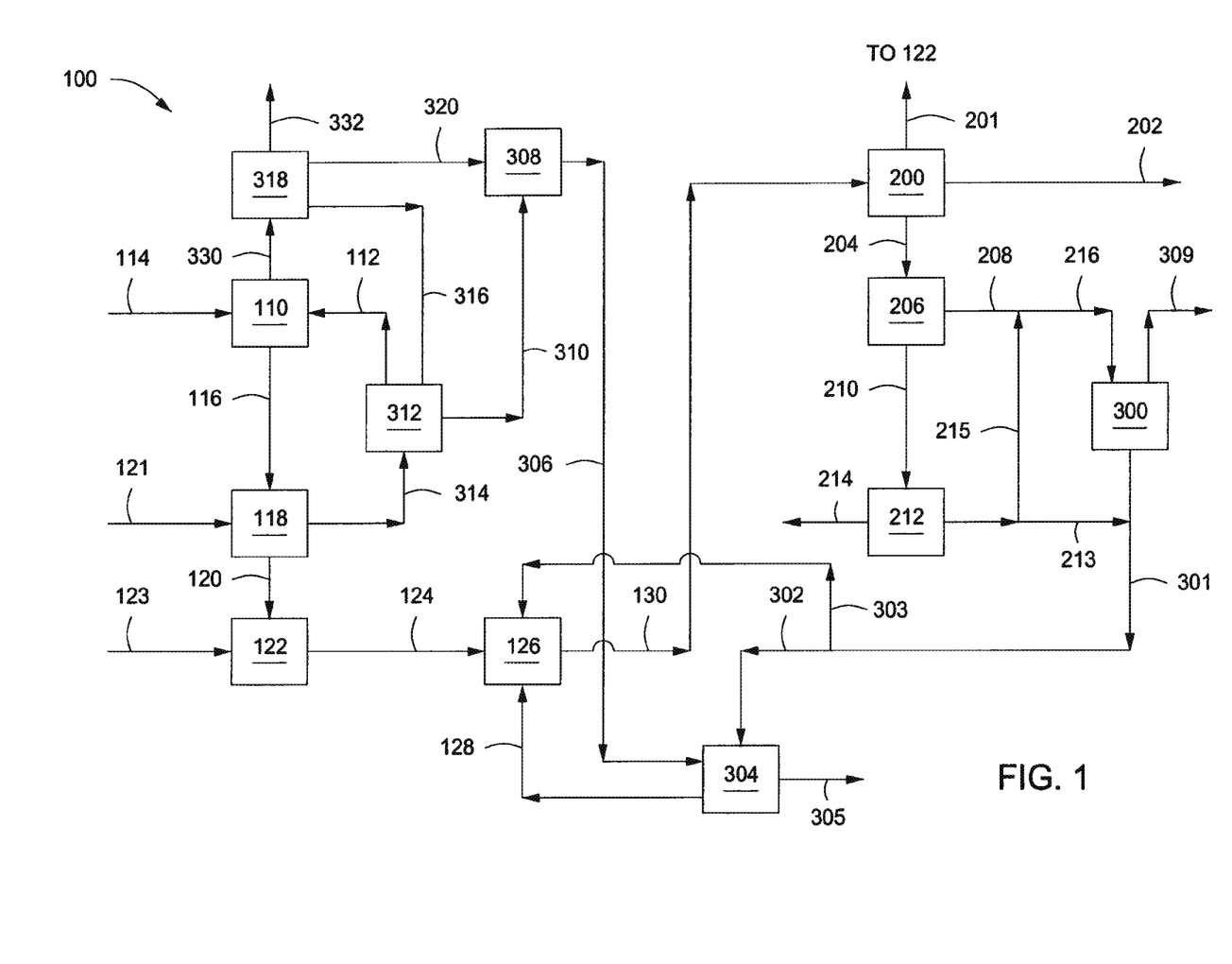
FIG. 1 depicts an illustrative system for producing acetone having a reduced methanol content, according to one or more embodiments described.

FIG. 1 depicts an illustrative system 100 for producing acetone, according to one or more embodiments. The system 100 can include one or more oxidation units 110 configured to receive cumene via line 112 and an oxidant via line 114 and to produce an oxidized product via line 116. The oxidation unit 110 can be any system or device suitable to provide oxygen to the cumene introduced via line 112. For example, the oxidation unit 110 can be one or more (e.g., a cascade) bubble columns (not shown). Further, the oxidant via line 114 can be added to the bottom of the bubble columns, such that oxygen transfers from the air bubbles into the cumene. Illustrative oxidants that can be introduced via line 114 to the oxidation unit 110 can include, but are not limited to, oxygen, air, ozone, or any combination or mixture thereof.

The oxidation reaction can produce methanol in the oxidized product in line 116. One such reaction can convert cumene and oxygen to methyl-phenyl-ketone (ACP) and methanol. Further, a portion of the methanol can be converted to methyl-hydrogen-peroxide (MHP). This can be additive to any methanol already in the cumene via line 112 introduced to the oxidation unit 110. The oxidized product via line 116 can include trace amounts of methanol. The oxidized product via line 116 can also include CHP. For example, the oxidized product via the line 116 can have a CHP concentration from a low of about 15 wt %, about 17 wt %, about 19 wt %, or about 21 wt % to a high of about 25 wt %, about 27 wt %, or about 30 wt %.

The oxidized product via line 116 can be introduced to one or more concentration units 118. The concentration unit 118 can include one or more vacuum distillation columns, heat exchangers, reflux drums, and other equipment. In such vacuum distillation columns, cumene can be separated at temperatures below about 100° C., for example. The concentration unit 118 can also receive cumene via a line 121, which can be introduced as reflux to one or more of the vacuum distillation columns to improve yield. The concentration unit 118 can produce a crude concentrated CHP product via line 120 and a stripped cumene product via line 314. The concentrated CHP product via line 120 can be methanol free with essentially all the methanol returned with the stripped cumene product via line 314.

The crude concentrated CHP product via line 120 can be introduced to one or more cleavage units 122. One or more acids, e.g., sulfuric acid, via line 123 can also be introduced to the cleavage unit 122. The cleavage unit 122 can include a back-mixed tank reactor (not shown) and/or a circulation loop reactor (not shown) with one or more heat exchangers included therein. The crude concentrated CHP product can be introduced to a back-mixed tank reactor and/or the circulation loop reactor to produce acetone and phenol. Further, the cleavage reaction is exothermic, thus the heat exchangers can be provided with cooling water or another heat exchange fluid to control the temperature of the reaction mixture in the cleavage unit 122. In the cleavage unit 122, DMBA can be partially dehydrated to AMS, which can react with phenol to form cumylphenols. AMS can also form high-boiling point dimers in the cleavage unit 122. DMBA reacts with CHP to form dicumyl peroxide (DCP) and water. Additional byproducts can also be produced, such as hydroxyacetone, 2-methylbenzofurane (2 MBF), and diacetone alcohol. These products can be fed to a plug-flow reactor (not shown), for example, at temperatures of about 100° C. or more. In the plug flow reactor, DCP can be converted to AMS, phenol and acetone, CHP can be cleaved to phenol and acetone, and/or DMBA can be dehydrated to AMS and water. At least a portion of these products can be discharged from the cleavage unit 122 as a crude product feed via line 124. One example of a cleavage unit can be as discussed and described in U.S. Pat. No. 5,371,305.

The cleavage unit 122 can generate small amounts of ACP and methanol. Such generated methanol can add to the methanol concentration of the crude product via line 124. The crude product via line 124 can be introduced to one or more neutralization units 126. The neutralization unit 126 can also receive one or more salt solutions via line 128. For example, the salt solution in line 128 can be or include sodium phenate. The salt solution can reduce or stop any continuing cleavage reactions in the crude product feed. Accordingly, the neutralization unit 126 can produce a neutralized crude product via line 130.

The neutralized crude product via line 130, which can include acetone and phenol, can be introduced to one or more acetone fractionation systems 200. The acetone fractionation system 200 can be or include one or more distillation columns. In the system 200, an acetone product can be recovered via lines 201 and 202. Although not shown, the acetone product via line 201 can be directed back or recycled to the cleavage unit 122. The addition of acetone to the cleavage unit 122 can raise or increase the AMS yield contained in the crude product via line 124 recovered therefrom. The acetone product via line 202 can be directed to a storage container, or can be otherwise stored, transported, and/or processed for subsequent use.

The acetone product via line 202 can have a methanol concentration from about 10 ppmw (parts per million by weight) to about 100 ppmw. For example, the acetone product via line 202 can have a methanol concentration from a low of about 10 ppmw, about 20 ppmw, about 30, ppmw about 40 ppmw, about 50 ppmw, about 55 ppmw, or about 60 ppmw to a high of about 65 ppmw, about 70 ppmw, about 80 ppmw, about 85 ppmw, about 90 ppmw, about 95 ppmw, about 100 ppmw. In another example, the methanol concentration in the acetone product via line 202 can be about 65 ppmw, about 70 ppmw, about 75 ppmw, about 80 ppmw, or about 85 ppmw. In another example, the methanol concentration in the acetone produce in via line 202 can be less than 100 ppmw, less than 90 ppmw, less than 80 ppm, less than 70 ppmw, less than 60 ppmw, or less than 50 ppmw. The acetone product flow rate via line 201 can be from a low of about 5 wt %, about 10 wt %, about 15 wt %, or about 20 wt % to a high of about 30 wt %, about 35 wt %, about 40 wt %, or about 45 wt % of the flow rate of the acetone product via line 202.

Figure 2:
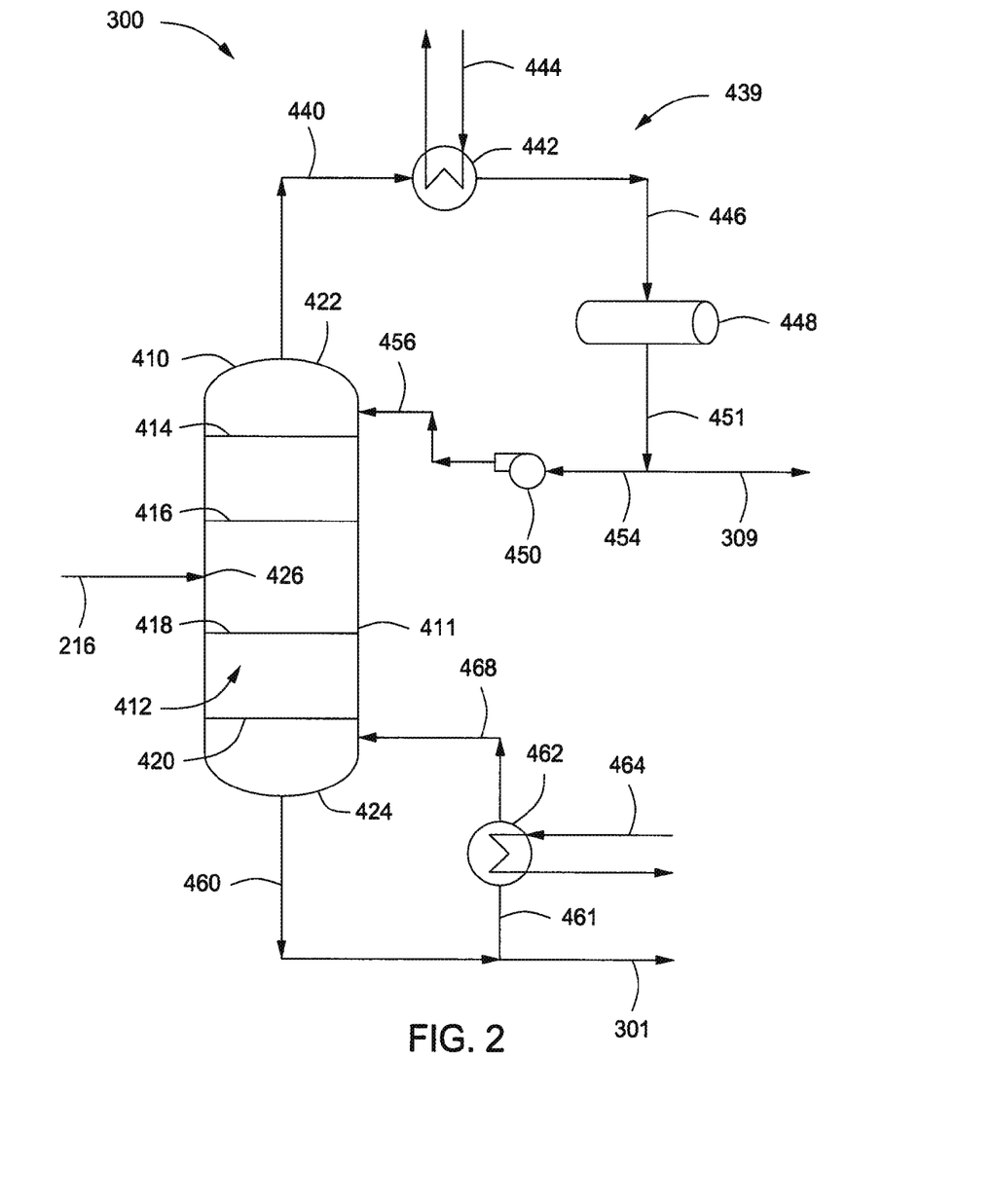
FIG. 2 depicts an illustrative methanol removal fractionation system, according to one or more embodiments described.

An acetone bottoms product via line 204 can be recovered from the acetone fractionation system 200 and can be introduced to one or more acetone bottoms separators 206. The acetone bottoms separator 206 can be or include one or more distillation columns, vacuum distillation columns, adsorption units, cyclonic separators, any combination thereof, or any other separation unit. The acetone bottoms separator 206 can separate the acetone bottoms product into an aqueous phenate product via lines 208 and a hydrocarbon crude AMS product via line 210. The crude AMS product or crude AMS via line 210 can be washed of residual caustic in one or more AMS wash units 212 to produce a washed crude AMS or washed AMS via line 214. The washed crude AMS via line 214 can be introduced into one or more AMS fractionation and/or hydrogenation systems (not shown) for AMS product recovery or hydrogenation to cumene for recycle to the oxidation unit 110. The aqueous streams from the crude AMS wash units 212 via line 215, or crude AMS wash water, can be combined with the aqueous phenate product via line 208 resulting in a process water that can be introduced to the methanol removal fractionation system 300 via line 216. The methanol removal fractionation system 300 can be or include one or more distillation columns or methanol removal columns (FIG. 2). At least a portion of the methanol entering the acetone fractionation system 200 can leave with the acetone bottoms aqueous phenate product via line 208. Any remaining methanol can leave with the crude AMS product via line 210 to be purged with any AMS light oils (not shown). For example, most of the methanol introduced to the acetone bottoms separator 206 can be removed with the aqueous phenate product via line 208 and a remainder of the methanol can be removed with the crude AMS product via line 210.

As used herein, the terms "fractionation column" and "column" refer to any system, device, or combination of systems and/or devices suitable for the selective separation of a mixture containing two or more components having differing boiling points. Such fractionation columns or columns can include, but are not limited to, dividing wall columns, scrub columns, distillation columns, rectification columns, and stripping columns.

The aqueous phenate product via line 208 can be introduced to the one or more methanol removal columns 300. In the absence of the methanol removal column 300, the phenate product, having higher amounts of methanol, acetone and light hydrocarbons, can be recycled via lines 213 and 301 to the neutralization unit 126 and/or dephenolation unit 304. The methanol removal column 300 can include one or more distillation columns, reflux drums, heat exchangers, and other equipment to remove at least a portion of the methanol from the aqueous phenate product in line 208. For example, the methanol removal column 300 can include a distillation column operated above the boiling temperature and pressure of methanol to remove methanol or methanol product via line 309 from the aqueous phenate product in line 208. The methanol, along with acetone and/or other hydrocarbons, can be recovered as a methanol product via line 309. A methanol-depleted product can be removed via line 301 and/or introduced via line 303 to the neutralization unit 126 and introduced via line 302 to one or more dephenolation units 304. The methanol-depleted product via line 301 can have a methanol concentration of less than 100 ppmw, less than 90 ppmw, less than 80 ppmw, less than 70 ppmw, less than 60 ppmw, less than about 50 ppmw, less than 40 ppmw, less than 30 ppmw, less than about 25 ppmw, less than 20 ppmw, less than 15 ppmw, less than about 10 ppmw, less than about 5 ppmw, or less than about 1 ppmw.

The methanol removal column 300 can reduce the methanol concentrations of the neutralized crude product via line 130 and the acetone bottoms product via line 204 in addition to reducing the methanol concentration in the acetone product via line 202. For example, introducing the aqueous phenate product via line 208 to the methanol removal column 300 can result in a reduction in methanol concentration of the neutralized crude product via line 130 of about 10 wt % about 20 wt %, about 30 wt %, or about 40 wt % to about 50 wt %, about 55 wt %, about 60 wt % or about 65 wt % compared to the methanol concentration of the neutralized crude product via line 130 when the phenate product is not introduced to the methanol removal column 300. In an example, introducing the aqueous phenate product via line 208 to the methanol removal column 300 can result in a reduction in methanol concentration of the acetone bottoms product via line 204 of about 10 wt %, about 20 wt %, about 30 wt %, or about 40 wt % to about 50 wt %, about 55 wt %, about 60 wt % or about 65 wt % compared to the methanol concentration of the acetone bottoms product via line 204 when the phenate product is not introduced to the methanol removal column 300. In another example, introducing the aqueous phenate product via line 208 to the methanol removal column 300 can result in a reduction in methanol concentration of the acetone product via line 202 of about 10 wt %, about 20 wt %, about 30 wt %, or about 40 wt % to about 50 wt %, about 55 wt %, about 60 wt % or about 65 wt % compared to the methanol concentration of the acetone product via line 202 when the phenate product is not introduced to the methanol removal column 300.

The methanol-depleted product via line 302 can be introduced to the dephenolation unit 304 to recover at least a portion of any phenol contained therein. The dephenolation unit 304 can also receive a decomposed MHP via line 306 from one or more MHP decomposer units 308. The dephenolation unit 304 can separate at least a portion of any phenol present in one or more feeds introduced thereto, and can recover the phenol as sodium phenate via line 128, for example. The sodium phenate via line 128 can then be introduced to the neutralization unit 126, as discussed and described above. The dephenolation unit 304 can also produce a waste water via line 305. The waste water via line 305 can have a methanol concentration ranging from a low of about 0.1 wt %, about 0.2 wt %, about 0.25 wt %, about 0.3 wt %, or about 0.34 wt % to a high of about 0.36 wt %, about 0.4 wt %, about 0.45 wt %, about 0.5 wt %, or about 0.6 wt %. An illustrative dephenolation unit can be as discussed and described in U.S. Pat. No. 6,824,687.

The MHP decomposer unit 308 can receive a spent caustic via line 310 from one or more cumene strip/wash units 312 and cumene via line 320 from one or more air separation units or spent air separation units 318. The MHP decomposer unit 308 can mix, blend, or otherwise contact the aqueous purge from the spent air separation unit 318 via line 320 with the spent caustic via line 310. The decomposition of the MHP can produce hydrogen, formic acid, formaldehyde, and water. The aqueous products from MHP decomposition can be directed to dephenolation via line 306.

The cumene strip/wash unit 312 can receive cumene via line 314 from the concentration unit 118 and/or cumene via line 316 from the spent air separation unit 318. The cumene strip/wash unit 312 can remove trace amounts of phenol and at least a portion of any organic acids, such as formic acid, formed in the oxidation unit 110 to improve oxidation reaction efficiency and to prevent corrosion on downstream sections. The cumene strip/wash unit 312 can include one or more drums and/or cumene extraction columns, where cumene hydro-peroxide (CHP) can be extracted using the cumene via line 314. The cumene strip/wash unit 312 can also receive cumene from the cumene via line 314 and/or the cumene via line 121 (not shown). The cumene strip/wash unit 312 can provide the cumene via line 112, which can be introduced to the oxidation unit 110, and spent caustic via line 310 to the MHP decomposer unit 308. An illustrative cumene wash unit can be as discussed and described in U.S. Pat. No. 5,220,103.

The spent air separation unit 318 can receive spent air via line 330 from the oxidation unit 110. The spent air via line 330 can have a methanol flow rate ranging from a low of about 20 kg/hr, about 25 kg/hr, about 30 kg/hr, about 35 kg/hr, or about 38 kg/hr to a high of about 40 kg/hr, about 45 kg/hr, about 50 kg/hr, about 55 kg/hr, or about 60 kg/hr. The spent air separation unit 318 can include one or more drums, adsorption units, distillation columns, cyclonic separators, and/or another structure configured to remove at least a portion of any hydrocarbons from the spent air via line 330. The spent air separation unit 318 can remove cumene and/or other hydrocarbons from the spent air via line 330. Cumene via line 316 can be obtained from the spent air separation unit and introduced to the cumene strip/wash unit 312 to obtain cumene via the aqueous purge via line 320. Cumene via the aqueous purge via line 320 can be introduced to the MHP decomposer 308. The spent air separation unit 318 can also produce a separated spent air via line 332.

FIG. 2 depicts an illustrative methanol removal fractionation system 300 for fractionating methanol, acetone and light hydrocarbons from process waters according to one or more embodiments. The methanol removal fractionation system 300 can include one or more fractionation columns 410. The fractionation column 410 (or "methanol removal column" ("MRC")) can include a shell or housing 411 disposed at any angle, in any configuration, and/or having any length to diameter (L/D) ratio. For clarity and ease of description, the fractionation column 410 will be further described with reference to a vertical, cylindrical, fractionation column 410 having an L/D ratio of greater than 1.

The fractionation column 410 can have a first or "top" end 422 and a second or "bottom" end 424. The process water via line 216 can be introduced into an interior volume 412 of the fractionation column 410 via a column inlet 426. The process water via line 216 can be from a single source or a combination of aqueous process streams such as the aqueous phenate product via line 208 and the crude AMS wash water via line 215. The process water via line 216 can also include (not shown) the neutralizer aqueous purge and the decomposed MHP via line 306. The fractionation column 410 can be heated, such that a thermal gradient can exist between the first and second ends 422, 424. Lower boiling point components of the process water via line 216 can be directed toward the first end 422, while the higher boiling point components thereof can be directed toward the second end 424. The lighter boiling point components can include methanol, acetone and light hydrocarbons such as aldehydes. At least a portion of the lower boiling point components of the process water via line 216 can be recovered via an overhead assembly 439. The overhead assembly 439 can include a condenser 442 and a line 440 fluidly coupled to the condenser 442 and to the fractionation column 410 proximal the first end 422. The lower boiling point components of the process water can be recovered via line 440 and introduced to the condenser 442. The condenser 442 can be any suitable type of heat exchanger, such as a shell-and-tube heat exchanger, a cross-flow heat exchanger, or the like. The condenser 442 can receive cooling water via line 444 to provide a heat transfer medium. The condenser 442 can thus condense at least a portion of the recovered light components via line 440 and produce condensed light components via line 446.

The condensed light components via line 446 can then be directed to one or more reflux drums 448, which can provide a "buffer" storage for the condensed light components. The condensed light components can be discharged via line 451. The condensed light components in line 451 can be split, apportioned, or otherwise divided into a distillate portion via line 309 and a reflux portion via line 454. The amount of the condensed light components provided as the distillate portion via line 452 as compared to the amount provided as the reflux portion via line 454 can be the same or different. The reflux portion via line 454 can be pumped via a pump 450 and recycled via line 456 to the interior volume 412 as reflux to increase yield performance. The distillate portion via line 309 can be combined with other light hydrocarbon purges from the recovery process (not shown) or disposed of separately. The fractionation column 410 can operated under pressure or under vacuum. For example, the fractionation column 410 can be operated under pressures of about 20 kPa, about 40 kPa, or about 60 kPa to about 100 kPa, about 120 kPa, or about 150 kPa.

A bottoms product via line 460 can be recovered from the second end 424 of the fractionation column 410. The bottoms product via line 460 can be introduced via line 461 to a reboiler 462. The reboiler 462 can be any type of heat exchanger, including a shell-and-tube heat exchanger, cross-flow heat exchanger, or the like. The reboiler 462 can also receive a heat exchange fluid via line 464. For example the heat exchange fluid via line 464 can be steam provided as an end or side product produced in any other system or device. The steam via line 464 can heat the bottoms product via line 461 in the reboiler 462 to produce a re-heated bottoms product via line 468. The reheated bottoms product via line 468 can then be returned to the fractionation column 410 to provide heat thereto. A portion of the bottoms product via line 460 can also be directed into line 301. As shown in FIG. 1, the bottoms product via line 301 can be introduced to the to the neutralization unit 126 via line 303 and/or the dephenolation unit 304 via line 302.

An interior volume 412 of the fractionation column 410 can be empty, partially filled, or completely filled with one or more fill materials (not shown). Illustrative fill materials can include, but are not limited to, trays, packing, or combinations thereof. For example, the fractionation unit 410 can include one or more trays (four are shown: 414, 416, 418, 420). The trays 414, 416, 418, 420 can be representative of four trays among a larger number of trays disposed in the interior volume 412. For example, the tray 414 can be from about the first tray from a first or "top" end 422 of the fractionation unit 410. The tray 416 can represent about the $2^{nd}$, $3^{rd}$, $4^{th}$, $5^{th}$, $10^{th}$, $15^{th}$, or greater, or any other number tray from the first end 422. For example, the total number of trays in the interior volume 412 can be about 10, about 15, about 20, about 25, or about 30. In a specific example, the total number of trays in the interior volume 412 can be about 24. In another example, the total number of trays disposed within the interior volume 412 can range from a low of about 5, about 10, about 15, about 20, or about 25 to a high of about 30, about 35, about 40, about 45, about 50, about 55, or about 60. The trays 418 and 420 can represent higher number trays; for example, the tray 420 can represent the tray nearest the second or "bottom" end 424 of the fractionation unit 410.

As used herein, the term "trays" can include, but is not limited to, one or more types of trays that can improve the contact between gas and liquid phases within the fractionation column 410. Illustrative trays can include, but are not limited to perforated trays, sieve trays, bubble cap trays, floating valve trays, fixed valve trays, tunnel trays, cartridge trays, dual flow trays, baffle trays, shower deck trays, disc and donut trays, orbit trays, horse shoe trays, cartridge trays, snap-in valve trays, chimney trays, slit trays, or any combination thereof.

As used herein, the term "packing material" can include, but is not limited one or more types of structured and/or random shaped material disposed within the fractionation column 410. The packing material can increase the effective surface area within the fractionation column 410, which can improve the mass transfer between liquid and gas phases within the fractionation column 410. The packing material can be made of any suitable material, for example metals, non-metals, ceramics, glasses, or any combination thereof. Illustrative examples of commercially available random packing material can include but is not limited to, IMTP®, INTALOX® ULTRA™, Raschig Rings, A-Pak Rings, saddle rings, Nutter Rings™, I-Rings™, C-Rings™, P-Rings™, R-Rings™, or any combination thereof. Illustrative examples of commercially available structured packing can include, but is not limited to, structured packing, corrugated sheets, crimped sheets, gauzes, grids, wire mesh, monolith honeycomb structures, or any combination thereof. For example, suitable structured packing can include but not limited to FLEXIPAC®, FLEXIPAC® HC®, INTERLOX®, Montz-Pak, Mellapak™, MellapakPlus™, GT-PAK™, GT-OP-TIM™ PAK, etc.

The fill material (e.g., trays 414, 416, 418, 420) can improve mass transfer and/or separation of a multi-component fluid. The fill material and/or the fill pattern in the interior volume 412 can include one or more structured and/or random packed materials. Two or more types of fill material can be disposed within the interior volume 412. For example, the interior volume 412 can contain random dumped packing beneath a feed introduction line or column inlet 426 and one or more trays above the column inlet 426.

The fractionation column 410 can be made of one or more metallic and/or non-metallic materials physically and chemically compatible with the temperature, pressure, and contents of the fractionation column 410. Suitable metallic materials can include, but are not limited to ferrous alloys including carbon and stainless steels, and non-ferrous alloys such as nickel, HASTELLOY®, INCONEL®, INCOLOY®, tantalum, and the like.

Further, the fractionation column 410 can be operated at a temperature sufficient to decrease the acetone content of the bottoms product via line 460; however, such temperature can also decrease the methanol content of the bottoms as well.

Figure 3:
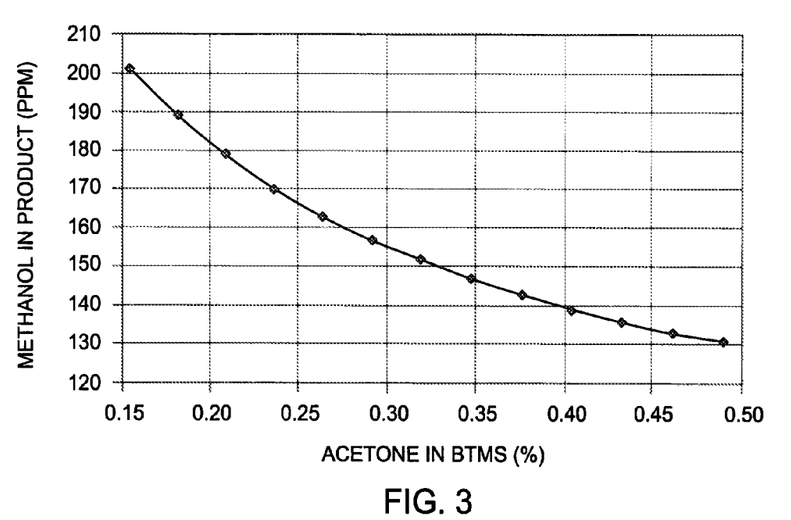
FIG. 3 is a graphical depiction of relationship between acetone in a bottoms product of an acetone fractionation column and methanol in an acetone product, according to one or more embodiments described.

FIG. 3 is a graphical depiction of a relationship between acetone in the bottoms product via line 460 (FIG. 2) of an acetone fractionation column and methanol in an acetone product via line 202 (FIGS. 1 and 2), according to one or more embodiments. As can be appreciated, an increase in acetone in the bottom product via line 460 can decrease methanol in the acetone product via line 202. This can lead to an increased resin catalyst life in downstream BPA production, for example.

Figure 4:
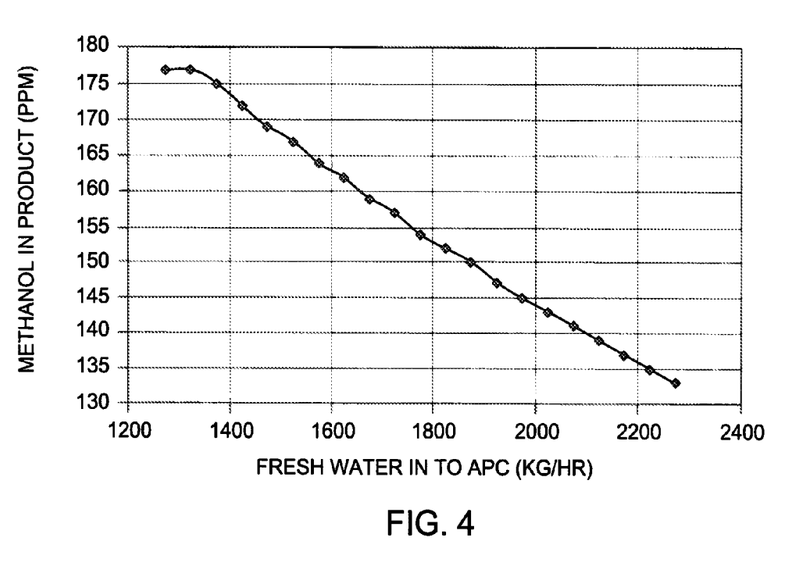
FIG. 4 is a graphical depiction of a relationship between water addition in an acetone fractionation column and methanol in an acetone product, according to one or more embodiments described.

FIG. 4 is a graphical depiction of a relationship between water addition in the acetone fractionation system 200 and methanol in the acetone product via line 202. As can be appreciated, an increase in the acetone recovered as bottoms via line 460 can decrease methanol concentration in the in the acetone product via line 202 (FIG. 1). This can lead to an increased resin catalyst life in downstream BPA production, for example. The methanol removal column 410 can allow for acetone fractionation system 200 operation with higher acetone content in the acetone bottoms product via line 204 and/or additional water addition to the acetone product column (APC) (not shown) in the acetone fractionation system 200. The methanol removal column 410 can substantially remove both the acetone and methanol content from the net aqueous purge via stream 208 thus reducing the downstream chemical loading on waste treatment facilities.

PROPHETIC EXAMPLES

Embodiments of the present invention can be further described with the following prophetic examples. Two simulated examples are provided. Example 1 is directed to a conventional system and method of acetone production from cumene, without a methanol removal column. Example 2 is directed to a system and method of acetone production from cumene, with a methanol removal column, as described above with regard to FIG. 1.

The methanol flow rates (in kg/hr) for an acetone production of about 19,930 kg/hr of acetone product summarized in the following Table. Since Example 1 does not include a methanol removal column, it does not include lines 208 and 309. Example 2 does include these lines, and they are shown in FIG. 1.

| Line No. (FIG. 1) | Example 1: Without Methanol Removal Column | Example 2: With Methanol Removal Column |
|---|---|---|
| 112: Cumene Strip/Wash Unit to Oxidation Unit | 68.87 | 68.87 |
| 116: Oxidation unit to Concentrator | 74.2 | 74.2 |
| 124: Cleavage Unit to Neutralization Unit | 8.04 | 5.29 |
| 128: Dephenolation Unit to Neutralization unit | 2.23 | 2.23 |
| 130: Neutralization unit to Acetone Fractionation Unit | 17.65 | 7.52 |
| 201: Acetone Fractionation Unit to Cleavage Unit | 1.51 | 0.76 |
| 202: Acetone Product from Acetone Fractionation Unit | 3.07 | 1.49 |
| 204: Acetone Fractionation Unit to Acetone Bottoms Separation Unit | 13.2 | 5.99 |
| 208: Acetone Bottoms Separation Unit to the Methanol removal column | NA | 5.99 |
| 303: Acetone Bottoms Separation Unit to the Neutralization Unit | 8.78 | <0.1 |
| 301: Discharge from Acetone Bottoms Separation | 13.1 | 5.99 |
| 302: Acetone Bottoms Separation Unit to the Dephenolation Unit | 4.32 | <0.1 |
| 306: MHP Decomposer Unit to Dephenolation Unit | 29.11 | 29.11 |
| 309: Methanol Discharge from the Methanol removal column | NA | 5.99 |
| 310: Cumene Strip/Wash Unit to MHP Decomposer Unit | 5.33 | 5.33 |
| 320: Spent Air Separation Unit to MHP Decomposer | 21.89 | 21.89 |
| 330: Oxidation Unit to Spent Air Separation Unit | 39.16 | 39.16 |
| 332: Spent Air outlet from Spent Air Separation Unit | 17.27 | 17.27 |

The Table illustrates that the methanol content in several lines of Example 2, and especially in lines 130, 204, 301, 302 and 303, is significantly reduced by the inclusion of the methanol removal column in Example 2. Further, the methanol in the acetone product can be reduced from about 150 ppmw in Example 1 to about 75 ppmw in Example 2. This can increase the useful life of downstream resin catalyst used to make BPA by about 50% or more.

Embodiments of the present disclosure further relate to any one or more of the following paragraphs:

1. A method for reducing methanol concentration in acetone, comprising: oxidizing and cleaving cumene to produce a crude acetone product; neutralizing the crude acetone product in a neutralization unit to produce a neutralized crude acetone product; fractionating the neutralized crude acetone product in an acetone fractionation column to produce an acetone product and an acetone bottoms product; removing methanol from the acetone bottoms product to produce a methanol-depleted product; and introducing the methanol-depleted product to the neutralization unit, a dephenolation unit, or both.

2. The method according to paragraph 1, wherein removing methanol from the acetone bottoms product comprises: separating at least a portion of the acetone bottoms product in a methanol removal column; and withdrawing a methanol product as an overhead and the methanol-depleted product as a bottoms from the methanol removal column.

3. The method according to paragraphs 1 or 2, wherein removing methanol from the acetone bottoms product comprises: introducing the acetone bottoms product to an acetone bottoms separator to obtain an aqueous phenate product and a crude AMS product; introducing the aqueous phenate product to a methanol removal column; and withdrawing a methanol product as overhead and the methanol-depleted product as a bottoms from the methanol removal column.

4. The method according to paragraph 3, further comprising: introducing the crude AMS product to an AMS wash unit to obtain a washed crude AMS and a crude AMS wash water; and wherein removing methanol from the acetone bottoms product further comprises: combining the aqueous phenate and the crude AMS wash water to obtain a process water; and introducing the process water to the methanol removal fractionation column.

5. The method according to any one of paragraphs 1 to 4, wherein a first portion of the methanol-depleted product is introduced to the neutralization unit and a second portion of the methanol-depleted product is introduced to the dephenolation unit.

6. The method according to any one of paragraphs 1 to 5, wherein the acetone product has a methanol concentration from about 10 ppmw to about 100 ppmw.

7. The method according to any one of paragraphs 1 to 6, wherein the acetone product has a methanol concentration of about 50 ppmw to about 100 ppmw.

8. The method according to any one of paragraphs 1 to 7, wherein the methanol-depleted product has a methanol concentration less than 100 ppmw.

9. The method according to any one of paragraphs 1 to 8, further comprising withdrawing a waste water comprising about 0.1 wt % to about 0.6 wt % methanol from the dephenolation unit.

10. A method for reducing methanol concentration in acetone, comprising: oxidizing and cleaving a cumene to produce a crude acetone product; neutralizing the crude acetone product in a neutralization unit to produce a neutralized crude acetone product; fractionating the neutralized crude acetone product in an acetone fractionation column to produce an acetone product having a methanol concentration of about 50 ppmw to about 100 ppmw and an acetone bottoms; introducing the acetone bottoms to an acetone bottoms separator to obtain an aqueous phenate product and a crude AMS product; introducing the aqueous phenate product to a methanol removal fractionation column; withdrawing a methanol product as an overhead and a methanol-depleted product as a bottoms from the methanol removal column; and introducing the methanol-depleted product to the neutralization unit, a dephenolation unit, or both.

11. The method according to paragraph 10, wherein a first portion of the methanol-depleted product is introduced to the neutralization unit and a second portion of the methanol-depleted product is introduced to the dephenolation unit.

12. The method according to paragraphs 10 or 11, wherein the methanol-depleted product has a methanol concentration of less than 100 ppmw.

13. The method according to any one of paragraphs 10 to 12, further comprising withdrawing a waste water comprising about 0.1 wt % to about 0.6 wt % methanol from the dephenolation unit.

14. The method according to any one of paragraphs 10 to 13, further comprising: introducing the crude AMS product to an AMS wash unit to obtain a washed crude AMS and a crude AMS wash water; combining the aqueous phenate product and the crude AMS wash water to obtain a process water; and introducing the process water to the methanol removal fractionation column.

15. A system for producing acetone, comprising: an oxidation unit configured to receive an oxidant and cumene and to produce an oxidized CHP product; a concentration unit fluidly coupled to the oxidation unit and configured to receive the oxidized CHP product and cumene and to produce a concentrated CHP product; a cleavage unit fluidly coupled to the concentration unit and configured to receive the concentrated CHP product therefrom and to produce a crude acetone product; a neutralization unit fluidly coupled to the cleavage unit and configured to receive the crude acetone product and produce a neutralized crude acetone product; an acetone fractionation column fluidly coupled to the neutralization unit and configured to receive the neutralized crude acetone product and to produce an acetone product and an acetone bottoms product; and a methanol removal column fluidly coupled to the acetone fractionation column and the neutralization unit, a dephenolation unit, or both, wherein the methanol removal column is configured to produce a methanol product and a methanol-depleted product; and one or more lines configured to introduce the methanol-depleted product to the neutralization unit, the dephenolation unit, or both.

16. The system according to paragraph 15, wherein the methanol removal column is configured to recover methanol, acetone and light hydrocarbon components from the acetone bottoms product in an overhead assembly.

17. The system according to paragraphs 15 or 16, wherein the concentration unit is configured to produce a cumene product and the concentrated CHP product.

18. The system according to paragraph 17, further comprising: a cumene strip/wash unit fluidly coupled to the concentration unit and the oxidation unit, the cumene strip/wash unit being configured to receive the cumene product from the concentration unit and provide the cumene for the oxidation unit and a waste water.

19. The system according to paragraph 18, wherein the acetone fractionation column is fluidly coupled to the cumene strip/wash unit to receive the waste water therefrom.

20. The system according to any one of paragraphs 15 to 19, wherein the acetone product has a methanol concentration of about 50 ppm to about 100 ppm.

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A method for reducing methanol concentration in acetone, comprising:
   oxidizing and cleaving cumene to produce a crude acetone product:
   neutralizing the crude acetone product in a neutralization unit to produce a neutralized crude acetone product;
   fractionating the neutralized crude acetone product in an acetone fractionation column to produce an acetone product and an acetone bottoms product;
   removing methanol from the acetone bottoms product to produce a methanol-depleted product; and
   introducing the methanol-depleted product to the neutralization unit, a dephenolation unit, or both.

2. The method of claim 1, wherein removing methanol from the acetone bottoms product comprises:
   separating at least a portion of the acetone bottoms product in a methanol removal column; and
   withdrawing a methanol product as an overhead and the methanol-depleted product as a bottoms from the methanol removal column.

3. The method of claim 1, wherein removing methanol from the acetone bottoms product comprises:
   introducing the acetone bottoms product to an acetone bottoms separator to obtain an aqueous phenate product and a crude AMS product;
   introducing the aqueous phenate product to a methanol removal column; and
   withdrawing a methanol product as overhead and the methanol-depleted product as a bottoms from the methanol removal column.

4. The method of claim 3, further comprising:
   introducing the crude AMS product to an AMS wash unit to obtain a washed crude AMS and a crude AMS wash water; and wherein removing methanol from the acetone bottoms product further comprises:
   combining the aqueous phenate and the crude AMS wash water to obtain a process water; and
   introducing the process water to the methanol removal fractionation column.

5. The method of claim 1, wherein a first portion of the methanol-depleted product is introduced to the neutralization unit and a second portion of the methanol-depleted product is introduced to the dephenolation unit.

6. The method of claim 1, wherein the acetone product has a methanol concentration from about 10 ppmw to about 100 ppmw.

7. The method of claim 1, wherein the acetone product has a methanol concentration of about 50 ppmw to about 100 ppmw.

8. The method of claim 1, wherein the methanol-depleted product has a methanol concentration less than 100 ppmw.

9. The method of claim 1, further comprising withdrawing a waste water comprising about 0.1 wt % to about 0.6 wt % methanol from the dephenolation unit.

10. A method for reducing methanol concentration in acetone, comprising:
    oxidizing and cleaving a cumene to produce a crude acetone product;
    neutralizing the crude acetone product in a neutralization unit to produce a neutralized crude acetone product;
    fractionating the neutralized crude acetone product in an acetone fractionation column to produce an acetone product having a methanol concentration of about 50 ppmw to about 100 ppmw and an acetone bottoms;
    introducing the acetone bottoms to an acetone bottoms separator to obtain an aqueous phenate product and a crude AMS product;
    introducing the aqueous phenate product to a methanol removal fractionation column;
    withdrawing a methanol product as an overhead and a methanol-depleted product as a bottoms from the methanol removal column; and
    introducing the methanol-depleted product to the neutralization unit, a dephenolation unit, or both.

11. The method of claim 10, wherein a first portion of the methanol-depleted product is introduced to the neutralization unit and a second portion of the methanol-depleted product is introduced to the dephenolation unit.

12. The method of claim 10, wherein the methanol-depleted product has a methanol concentration of less than 100 ppmw.

13. The method of claim 10, further comprising withdrawing a waste water comprising about 0.1 wt % to about 0.6 wt % methanol from the dephenolation unit.

14. The method of claim 10, further comprising:
    introducing the crude AMS product to an AMS wash unit to obtain a washed crude AMS and a crude AMS wash water;
    combining the aqueous phenate product and the crude AMS wash water to obtain a process water; and
    introducing the process water to the methanol removal fractionation column.

15. A system for producing acetone, comprising:
    an oxidation unit configured to receive an oxidant and cumene and to produce an oxidized CHP product;
    a concentration unit fluidly coupled to the oxidation unit and configured to receive the oxidized CHP product and cumene and to produce a concentrated CHP product;
    a cleavage unit fluidly coupled to the concentration unit and configured to receive the concentrated CHP product therefrom and to produce a crude acetone product;
    a neutralization unit fluidly coupled to the cleavage unit and configured to receive the crude acetone product and produce a neutralized crude acetone product;
    an acetone fractionation column fluidly coupled to the neutralization unit and configured to receive the neutralized crude acetone product and to produce an acetone product and an acetone bottoms product; and
    a methanol removal column fluidly coupled to the acetone fractionation column and the neutralization unit, a dephenolation unit, or both, wherein the methanol removal column is configured to produce a methanol product and a methanol-depleted product; and
    one or more lines configured to introduce the methanol-depleted product to the neutralization unit, the dephenolation unit, or both.

16. The system of claim 15, wherein the methanol removal column is configured to recover methanol, acetone and light hydrocarbon components from the acetone bottoms product in an overhead assembly.

17. The system of claim 15, wherein the concentration unit is configured to produce a cumene product and the concentrated CHP product.

18. The system of claim 17, further comprising:
    a cumene strip/wash unit fluidly coupled to the concentration unit and the oxidation unit, the cumene strip/wash unit being configured to receive the cumene product from the concentration unit and provide the cumene for the oxidation unit and a waste water.

19. The system of claim 18, wherein the acetone fractionation column is fluidly coupled to the cumene strip/wash unit to receive the waste water therefrom.

20. The system of claim 15, wherein the acetone product has a methanol concentration of about 50 ppm to about 100 ppm.

* * * * *